United States Patent
Durand et al.

(10) Patent No.: US 10,166,540 B2
(45) Date of Patent: Jan. 1, 2019

(54) GAS EVACUATION SYSTEM FOR NANOFLUIDIC BIOSENSOR

(71) Applicant: Abionic SA, Lausanne (CH)

(72) Inventors: Nicolas Durand, Blonay (CH); Iwan Maerki, Yverdon-les-Bains (CH); Matthias Geissbuehler, Lausanne (CH)

(73) Assignee: Abionic SA, Epalinges (CH)

( * ) Notice: Subject to any disclaimer, the term of this patent is extended or adjusted under 35 U.S.C. 154(b) by 229 days.

(21) Appl. No.: 15/103,866

(22) PCT Filed: Dec. 17, 2014

(86) PCT No.: PCT/IB2014/066102
§ 371 (c)(1),
(2) Date: Jun. 11, 2016

(87) PCT Pub. No.: WO2015/087178
PCT Pub. Date: Jun. 18, 2015

(65) Prior Publication Data
US 2016/0339432 A1    Nov. 24, 2016

(30) Foreign Application Priority Data

Dec. 13, 2013 (WO) .................. PCT/IB2013/060935

(51) Int. Cl.
| | | |
|---|---|---|
| *G01N 33/558* | (2006.01) | |
| *B01L 3/00* | (2006.01) | |
| *G01N 21/05* | (2006.01) | |
| *G01N 21/64* | (2006.01) | |
| *G01N 33/497* | (2006.01) | |

(52) U.S. Cl.
CPC ........ *B01L 3/502723* (2013.01); *G01N 21/05* (2013.01); *G01N 21/6428* (2013.01);
(Continued)

(58) Field of Classification Search
None
See application file for complete search history.

(56) References Cited

U.S. PATENT DOCUMENTS

| | | |
|---|---|---|
| 8,938,103 B2 | 1/2015 | Durand et al. |
| 9,452,927 B2 | 9/2016 | Durand et al. |

(Continued)

FOREIGN PATENT DOCUMENTS

| | | |
|---|---|---|
| JP | H9-257748 | 10/1997 |
| WO | WO 2011/064701 | 6/2011 |
| WO | WO 2011/107916 | 9/2011 |
| WO | WO 2012/120387 | 12/2012 |

OTHER PUBLICATIONS

International Search Report dated Mar. 24, 2015.
(Continued)

*Primary Examiner* — Christopher L Chin
(74) *Attorney, Agent, or Firm* — Andre Roland S.A.; Nikolaus Schibli

(57) ABSTRACT

A nanofluidic biosensor system (200) comprising a bottom substrate (120) and a top substrate (110) between which are defined an input lateral aperture (210), a nanoslit (230) which contains at least one functionalized area (231) and an output lateral aperture (220) or an internal reservoir (221), said biosensor system (200) being adapted to let a solution containing biomolecules (320) enter the input lateral aperture (210) and successively pass through said nanoslit (230) and said output lateral aperture (220) or internal reservoir (221); said biosensor system (200) furthermore comprising a gas evacuation subsystem (150-155) which is located between said nanoslit (230) and the biosensor external environment.

12 Claims, 4 Drawing Sheets

(52) U.S. Cl.
CPC ......... *G01N 33/497* (2013.01); *G01N 33/558* (2013.01); *B01L 2200/0631* (2013.01); *B01L 2200/0684* (2013.01); *B01L 2300/069* (2013.01); *B01L 2300/0636* (2013.01); *B01L 2300/0816* (2013.01); *B01L 2300/0822* (2013.01); *B01L 2300/0851* (2013.01); *B01L 2300/0887* (2013.01); *B01L 2300/0896* (2013.01); *B01L 2400/0406* (2013.01); *G01N 2021/054* (2013.01)

(56) References Cited

U.S. PATENT DOCUMENTS

| | | | |
|---|---|---|---|
| 9,547,004 B2 | 7/2017 | Durand et al. | |
| 2005/0266582 A1* | 12/2005 | Modlin | B01L 3/5027 436/164 |
| 2017/0197210 A1 | 7/2017 | Maerki et al. | |

OTHER PUBLICATIONS

Meng et al., "A degassing plate with hydrophobic bubble capture and distributed venting for microfluidic devices." Journal of Micromechanics and Microengineering 16.2 (2006): 419.

Written Opinion of the International Search Authority dated Mar. 24, 2015.

Japanese Office Action for the counterpart JP case witn the Serial No. 2016-558438 dated Aug. 7, 2018 and English Translaton thereof.

* cited by examiner

US 10,166,540 B2

GAS EVACUATION SYSTEM FOR NANOFLUIDIC BIOSENSOR

CROSS REFERENCE TO RELATED APPLICATIONS

The present application is a U.S. national stage application of International patent application PCT/IB2014/066102 filed on Nov. 17, 2014 that designated the United States, and claims foreign priority to International patent application PCT/IB2013/060935 filed on Dec. 13, 2013, the contents of both documents being herewith incorporated by reference in their entirety.

FIELD OF INVENTION

The present invention relates to nanofluidic biosensors with at least one lateral aperture. This kind of biosensor may advantageously be used for accurate rapid quantification of biomedical and biological samples.

BACKGROUND OF THE INVENTION

Nanofluidic biosensors are defined as fluidic systems with nanometer-sized confinements and/or lateral apertures. Applications include quantification of the presence of biomolecules in a solution. A majority of the current nanofluidic biosensor developments are intended for bioengineering and biotechnology applications. In the scope of this invention, biosensors are used to quantify the presence of biomolecules in solution for in vitro diagnostic applications.

Swiss patent application CH 01824/09 discloses biosensors with lateral apertures for the detection of biomolecular interactions, PCT application IB2010/050867 discloses their use with simple optical systems and PCT application IB2012/050527 discloses the method to decrease the incubation time and to increase the sensitivity of the described biosensors. The diffusion of biomolecules in these configurations are slow and require either long waiting times to attain stable measurement conditions or highly concentrated solutions for the observation of the biomolecular interactions.

Biomarkers, also called biological markers, are substances used as specific indicators for detecting the presence of biomolecules. It is a characteristic that is objectively measured and evaluated as an indicator of biological processes, pathogenic processes, or pharmacologic responses to a therapeutic intervention.

Current practices for the detection of specific biomolecules can be divided in two categories: (a) the labeled techniques and (b) the label-free techniques.

Among the labeled techniques, the widely used are fluorescence, colorimetry, radioactivity, phosphorescence, bioluminescence and chemiluminescence. Functionalized magnetic beads can also be considered as labeling techniques. Labeled techniques advantages are the sensitivity in comparison to label-free methods and the molecular recognition due to specific labeling.

Among the label-free techniques, the widely used are electrochemical biosensors, referring to amperometric, capacitive, conductometric or impedimetric sensors, which have the advantage of being rapid and inexpensive. They measure the change in electrical properties of electrode structures as biomolecules become entrapped or immobilized onto or near the electrode, but all these concepts lack molecular specific contrast, sensitivity and reliability.

Enzyme linked immunosorbent assay (ELISA) is an important biochemical technique mainly used to detect the presence of soluble biomolecules in serum, and thus is widely used as diagnostic tool in medicine and quality control check in various industries. ELISA analysis are however expensive, require large amounts of solution and is time consuming.

The other important technologies for biomolecular diagnostics are Western and Northern blots, protein electrophoresis and polymerase chain reaction (PCR). However, these methods require highly concentrated analytes and do not allow high throughput samples testing.

OBJECTIVES

It is an object of this invention to improve the variability of rapid nanofluidic biosensors, which do not require complex manipulations.

Still another object of the invention is to create crossing-through galleries allowing the evacuation of gas that may be trapped inside the biosensor during its filling by the solution to analyze.

Still another object of the invention is to enhance the sensitivity of the detection by forcing a higher volume for solution to flow through the biosensor entry (nanoslit).

SUMMARY OF THE INVENTION

This invention is based on the discovery that several air bubbles can appear in a nanofluidic biosensor if the filling front is not perfectly homogenous. In order to evacuate the air trapped, a gas evacuation subsystem allowing the air to exit the biosensor has been invented.

This invention is also based on the discovery that removing air bubbles is strongly improving the variability inter-biosensors as well as the sensitivity.

This gas evacuation subsystem according to the invention may be made of porous material.

Furthermore, this invention highlights the possibility to locally structure one or both of the biosensor substrates in order to define a gas evacuation subsystem.

In the present text the term "gas evacuation subsystem" has to be understood as any system which may be used for the intended purpose. For instance it may be made of pores, crossing-through holes or slits.

In the scope of this invention, nanofluidics is used because of its high surface-to-volume ratio, meaning that the surfaces included in the detection volume, maximize the probability of the interactions between biomolecules and immobilized biomarkers on surfaces. It also strongly reduces the background signal of the solution due to the small portion of substrate that is within the detection volume.

The invention therefore relates to a biosensor as defined in the claims.

It also relates to an assembly and a method using said biosensor. Some non-limiting examples of the invention are presented in the following chapters. Some of those examples are illustrated.

DETAILED DESCRIPTION OF THE INVENTION

As used herein, the term "biomolecules" is intended to be a generic term, which includes for example (but not limited to) proteins such as antibodies or cytokines, peptides, nucleic acids, lipid molecules, polysaccharides and virus.

As used herein, the terms "nanoslit" is intended to be a generic term, which means well-defined microfabricated structure with at least one nanometer-sized dimension. The nanometer-sized dimension of the nanoslit is defined to be higher than 2 nm because of the size of the smallest biomolecules to be detected that have to enter into the slit and that are in the same order of magnitude. The present invention is limited to nanoslits with a height lower than few microns, because of the range of the detection volume of the optical system that are typically in the same order of magnitude.

As used herein, the term "lateral aperture" is intended to be a generic term, which includes for example (but not limited to) input and output channels.

As used herein, the term "internal reservoir" is intended to be a generic term, which includes for example (but not limited to) spaces that don't have a direct access to a lateral aperture, but being in contact with the gas evacuation system.

Figure 1A:
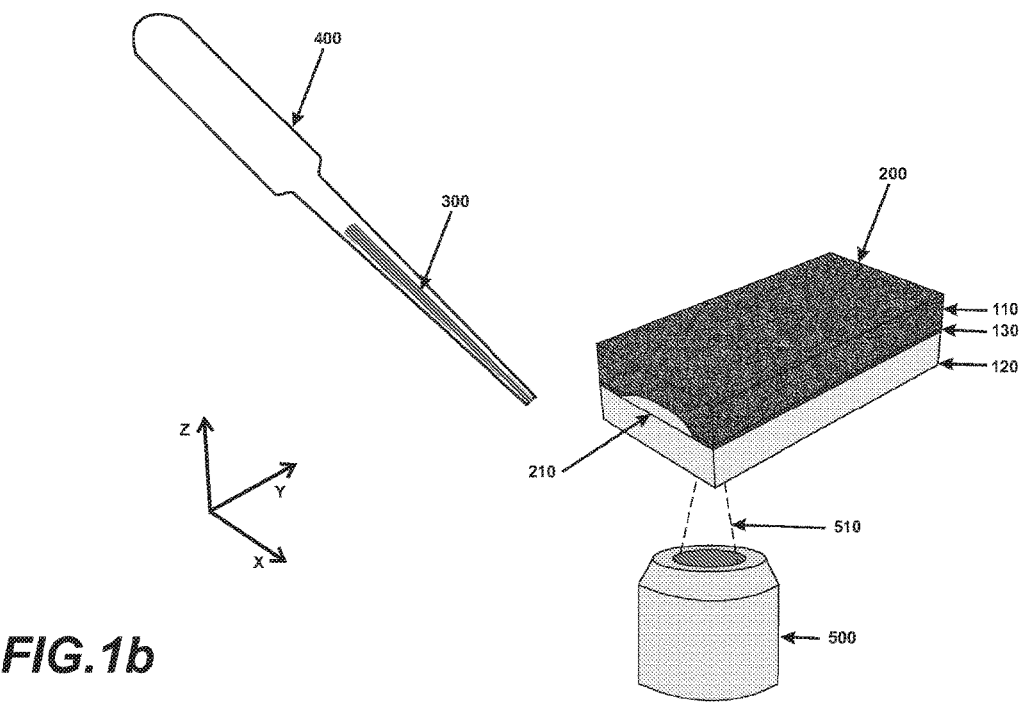
FIG. 1a is a perspective view of a nanofluidic biosensor system composed of a bottom substrate 120 a spacer layer 130 and a top substrate 110 containing structured or non-structured crossing pores, and a lateral aperture 210. A solution 300 containing fluorescently-labeled biomolecules is deposited by a pipet system 400 in a way that the solution is entering inside the biosensor from the lateral aperture 210. An optical system 500 based on a laser beam 510 is typically used for the measurement.
Figure 1B:
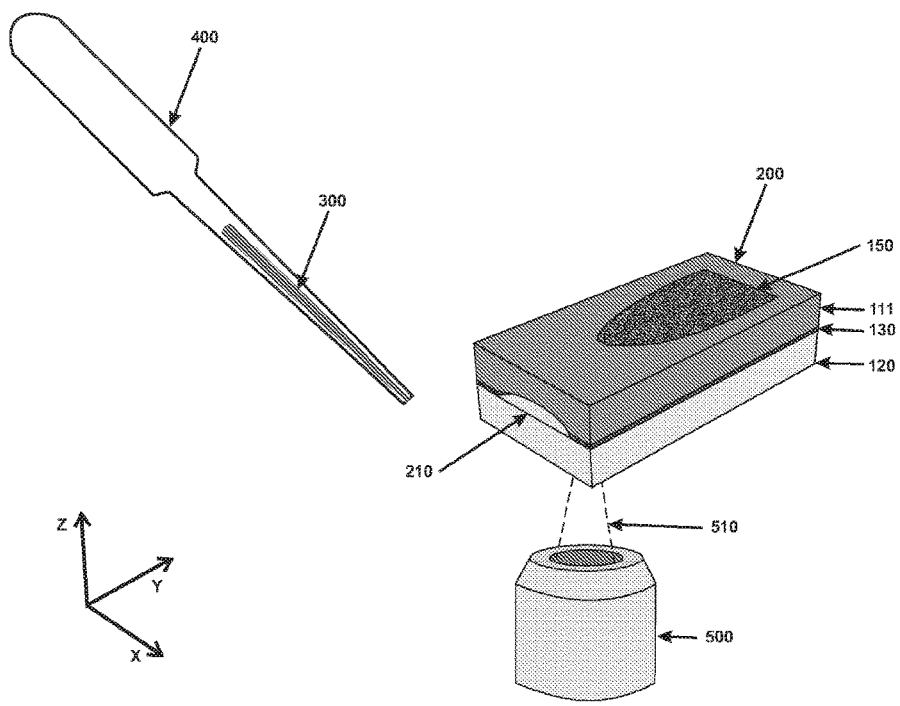
FIG. 1b is a perspective view of a nanofluidic biosensor system composed of a bottom substrate 120 a spacer layer 130 and a top substrate 111 containing structured or not structured crossing pores at defined position 150, and a lateral aperture 210. A solution 300 containing fluorescently-labeled biomolecules is deposited by a pipet system 400 in a way that the solution is entering inside the biosensor from the lateral aperture 210. An optical system 500 based on a laser beam 510 is typically used for the measurement.

The present invention aims to enhance the filling of the output lateral aperture 220 or the internal reservoir 221 thanks to a system of gas evacuation that guarantees a low interbiosensor variability of biomolecules concentration measurement. As shown in FIG. 1a and FIG. 1b, a nanofluidic biosensor composed of a substrate 110 or 111 and a substrate 120 sandwiched together with a spacer 130, and having an input lateral aperture 210, is immobilized above an optical unit 500. The substrate 110 may be porous, and the substrate 111 may have locally structured cross-through pores, in order to allow the gas evacuation during the filling of the nanofluidic biosensor. A mix solution 300 containing the biomolecules of interest is disposed at the input lateral aperture 210 by a pipet system 400. Finally, an optical unit 500 is used to measure the biomolecular interactions inside the biosensors 200 by focusing the laser beam 510 inside the biosensors nanoslit.

Figure 2A:
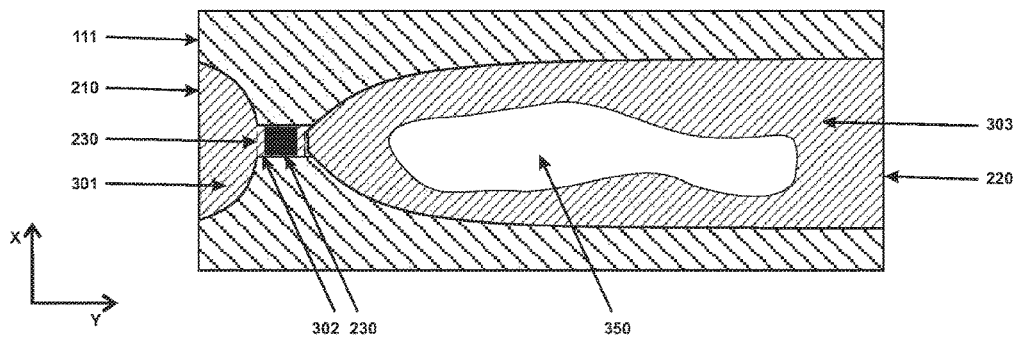
FIG. 2a shows a top view cross section of the substrate 111 composing a nanofluidic biosensor. An input lateral aperture 210, a nanoslit 230 and an output aperture 220 is composing the fluidic system. The measurement area 231 is defined inside the nanoslit. Once the system has reached its equilibrium, solution may be found in the input lateral aperture 301, the nanoslit 302 and the output lateral aperture 303. Gas bubble 350 may be formed if the solution flow front actuated by the liquid-driving component 140 is not perfectly uniform.
Figure 2B:
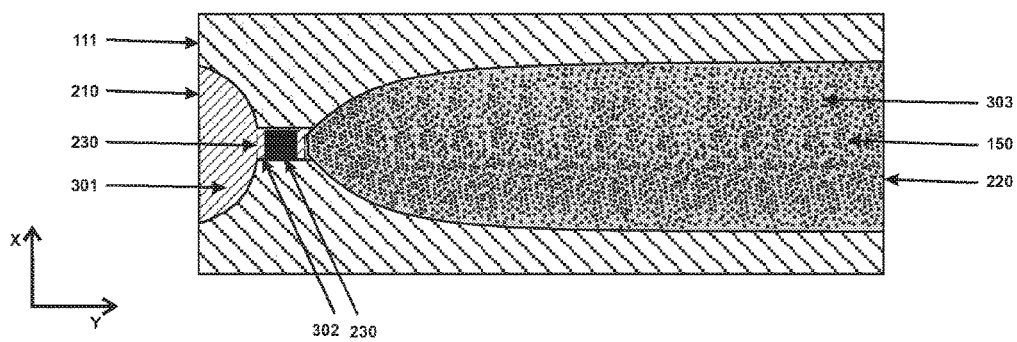
FIG. 2b shows a top view cross section of the substrate 111 composing a nanofluidic biosensor. An input lateral aperture 210, a nanoslit 230 and an output aperture 220 is composing the fluidic system. The measurement area 231 is defined inside the nanoslit 230, and the substrate crossing-through pores 150 are defined directly inside the output lateral aperture 220. A liquid-driving component 140 is also present inside the output lateral aperture 220. Once the system has reached its equilibrium, solution may be found in the input lateral aperture 301, the biosensor entry (nanoslit) 302 and the output lateral aperture 303. Gas bubbles are not present as the gas can exhaust through the pores system 150.

FIG. 2a and FIG. 2b illustrate top views of half a nanofluidic biosensor composed of a substrate 111 containing an input lateral aperture 210 and an output lateral aperture 220, linked together by a nanoslit 230. In FIG. 2a, the output lateral aperture 220 is not designed with a gas evacuation system whereas in FIG. 2b, the output lateral aperture 220 is structured with a gas evacuation system 150 which can be obtained with a local dry or wet chemical etching process in order to obtain cross-through pores or holes. When a solution containing biomolecules is deposited at the input lateral aperture 210, the solution will fill firstly the input lateral aperture 301, fill the nanoslit 302 and then finally fill the output lateral aperture 303. Despite of an excellent liquid-driving system 140, the filling of the output lateral aperture 220 is rarely uniform. Typically, the solution may reach uniformly the border of the aperture 220 and after stopping due to surface tensions equilibrium, it can block gas inside the output lateral aperture 220. This can lead to the apparition of gas bubbles 350 due to the fact that gas cannot exhaust by the lateral aperture 210 or 220. As depicted in FIG. 2b, gas may exhaust the system through cross-through pores 150, avoiding the apparition of gas bubbles and guaranteeing the full filling of the output lateral aperture, and thus ensuring low interbiosensor variability.

Figure 3A:
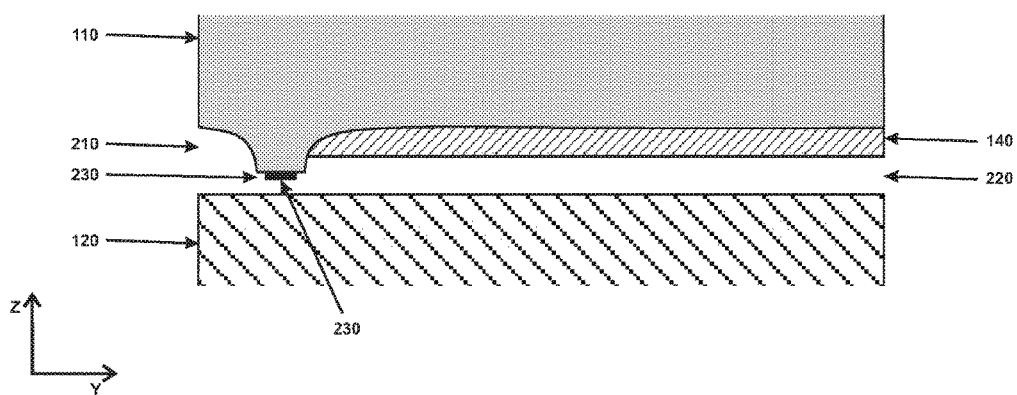
FIG. 3a shows a lateral cross section of the nanofluidic biosensor defined by two substrates 110 and 120, and composed by an input lateral aperture 210 and an output lateral aperture 220 linked together by a nanoslit 230. The output lateral aperture 220 may contain a liquid driving system 140. The substrate 110 is entirely porous with crossing-through pores.
Figure 3B:
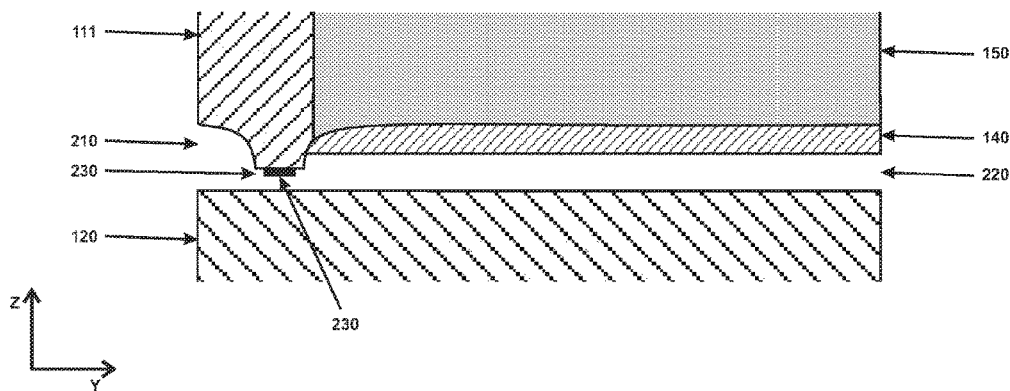
FIG. 3b shows a lateral cross section of the nanofluidic biosensor defined by two substrates 111 and 120, and composed by an input lateral aperture 210 and an output lateral aperture 220 linked together by a nanoslit 230. The output lateral aperture 220 may contain a liquid driving system 140. The substrate 111 may be structured to be locally porous with crossing-through pores 150.
Figure 3C:
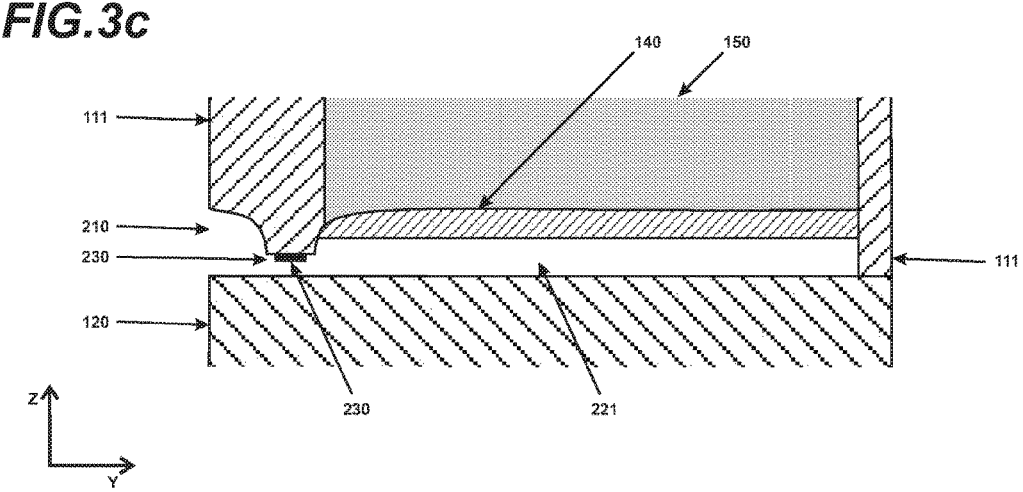
FIG. 3c shows a lateral cross section of the nanofluidic biosensor defined by two substrates 111 and 120, and composed by an input lateral aperture 210 and an internal reservoir 221 linked together by a nanoslit 230. The internal reservoir 221 may contain a liquid driving system 140. The substrate 111 may be structured to be locally porous with crossing-through pores 150.
Figure 3D:
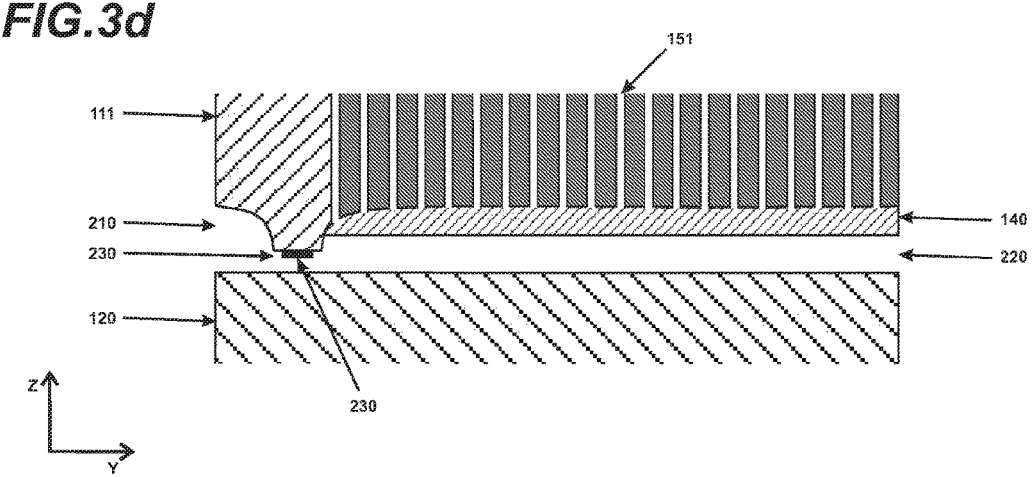
FIG. 3d shows a lateral cross section of the nanofluidic biosensor defined by two substrates 111 and 120, and composed by an input lateral aperture 210 and an output lateral aperture 220 linked together by a nanoslit 230. The output lateral aperture 220 may contain a liquid driving system 140. The substrate 111 may be locally structured with crossing-through holes or slits 151.
Figure 3E:
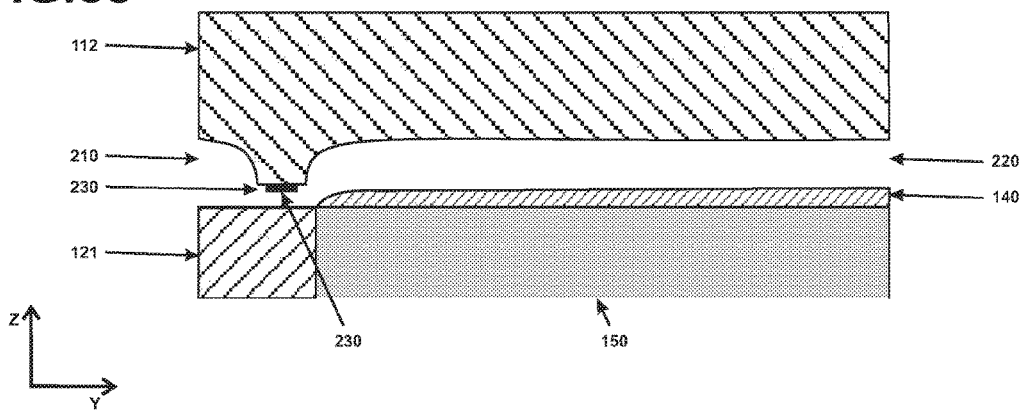
FIG. 3e shows a lateral cross section of the nanofluidic biosensor defined by two substrates 111 and 120, and composed by an input lateral aperture 210 and an output lateral aperture 220 linked together by a nanoslit 230. The output lateral aperture 220 may contain a liquid driving system 140. The substrate 121 may be structured to be locally porous with crossing-through pores 150.

FIGS. 3a, 3b, 3c, 3d and 3e illustrate different configurations of nanofluidic biosensor with lateral apertures and gas evacuation system according to the invention. The system, presented as lateral cross views, is composed of a nanoslit 230 linking an input lateral aperture 210 with either an output lateral aperture 220, either an internal reservoir 221. A driving component 140 is structured next or inside the output lateral aperture 220. In FIG. 3a, the biosensor is composed of a substrate 110 that is entirely porous with cross-through galleries. FIG. 3b presents an alternative where the substrate 111 is locally structured with porous cross-through galleries 150. FIG. 3c illustrates the case where there is no output lateral aperture as the gas can exhaust through the porous areas 150 locally structured in the substrate 111 as the solution is filling the system. FIG. 3d presents the case where the substrate 111 is locally structured with crossing-through holes 151 with nano-, micro- or millimeter dimensions. Finally FIG. 3e illustrates that the gas evacuation system 150 may be structured on the other substrate 121, or on both substrates 112 and 121.

Figure 4:
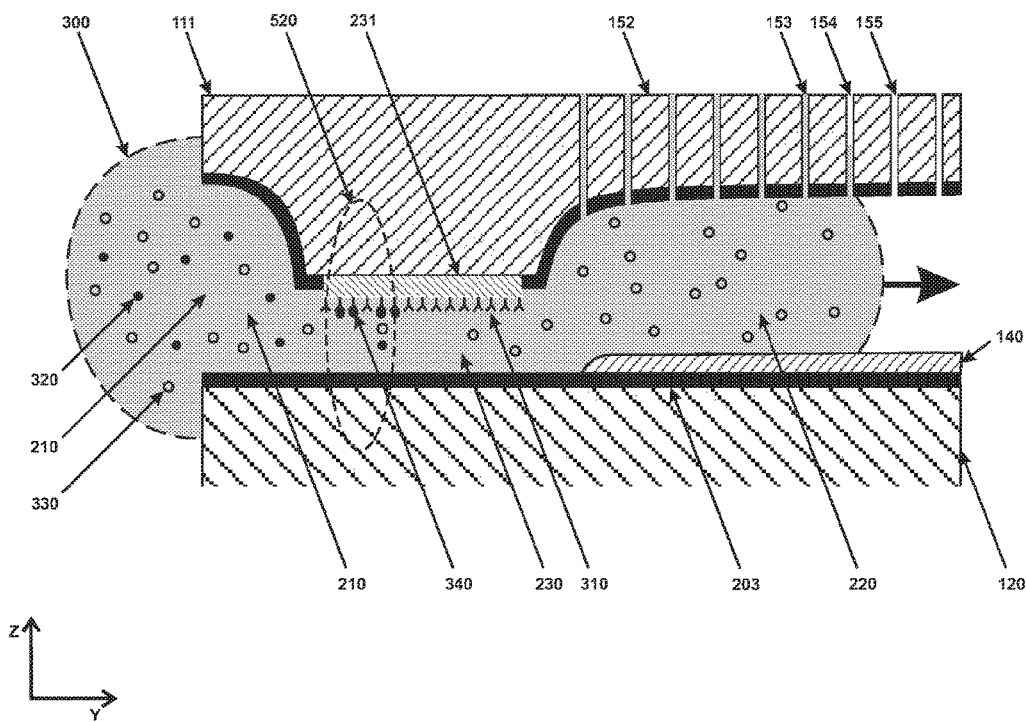
FIG. 4 shows a lateral cross section of the nanofluidic biosensor defined by two substrates 111 and 120, and composed by an input lateral aperture 210 and an output lateral aperture 220 linked together by a nanoslit 230. Only one of the substrates is locally structured by area 231 that is functionalized by biomarkers 310 and other areas 203 that prevent that functionalization. Reagent solution 300 containing biomolecules enter the nanoslit 230 from the input lateral aperture 210 to the output lateral aperture 220 and is actuated by the internal driving component 140. When reaching the output lateral aperture 220, the solution 300 containing the molecules to detected 320 and other molecules 330 is filling the structured cross-through pores 152. The figure shows fully filled pores 153, pores that are being filled 154 and pores to be filled 155. The laser beam 510 monitors the concentration of the immobilized biomolecules 340 in the detection volume 520.

FIG. 4 illustrates the principle of detection and the cross-section of a biosensor with lateral apertures and gas evacuation system according to the invention. The system presented as a lateral cross view is composed of a nanoslit 230 linking an input lateral aperture 210 with an output lateral output aperture 220. A liquid-driving component 140 is located next or inside the output lateral aperture 220. The gas evacuation system 152 is also present in the output lateral aperture 220. First, biomarkers 310 are immobilized on selectively functionalized nanoslit surfaces of one or both substrates 111 and 120. The other nanoslit surfaces and the lateral aperture surfaces may be protected by the deposition of a non-functionalized layer 203 in order to prevent non-specificity. Once the solution 300 containing the fluorescently labeled specific biomolecules 320 and non-specific biomolecules 330 is deposited at the input lateral aperture, it fills the system from the input lateral aperture 210 to the output lateral aperture 220 through the nanoslit 230. After filling the nanoslit 230 and when reaching the liquid-driving component 140, the solution 300 fills the output lateral aperture 220. When flowing through the nanoslit 230, and thanks to Brownian motion, specific biomolecules 320 interact with the biomarkers 310 immobilized inside the nanoslit 230 and form molecular complexes 340. The non-specific biomolecules 330 will also flow through the nano slit 230 but will not form molecular complexes with the immobilized biomarkers 310 and will continue into the output lateral aperture 220. When the solution 300 is in contact with the gas evacuation system 152, the liquid will enter into crossing-through pores 155, with a transitory filling state 154, until it has completely filled the pores 153. Finally, after having reached an equilibrium state, the immobilized fluorescently emitting complexes 340 and the diffusing fluorescently emitting biomolecules 330 diffusing across the optical detection volume are excited by the laser beam 510 and both detected by the optical system.

According to the present invention, the device offers great improvements in variability and sensitivity for the detection, enumeration, identification and characterization of biomolecules interacting or not with other immobilized biomolecules. Applications of the present invention can cover biomedical, biological or food analysis as well as fundamental studies in analytical and bioanalytical chemistry.

The invention claimed is:

1. A nanofluidic biosensor system comprising:
a bottom substrate and a top substrate;
arranged along a flow direction of the biosensor system between the bottom substrate and the top substrate, (i) an input lateral aperture, (ii) a nanoslit having a functionalized area, and then (iii) at least one of an output lateral aperture and an internal reservoir; and
a gas evacuation subsystem located at at least one of the output lateral aperture and the internal reservoir, along the flow direction located between the nanoslit and an external environment of the biosensor downstream of the nanoslit,
wherein the gas evacuation subsystem evacuates trapped air from the nanofluidic biosensor system.

2. The nanofluidic biosensor system according to claim 1 further comprising:
a liquid driving subsystem located between the nanoslit and the gas evacuation subsystem to actuate a reagent solution in the biosensor system.

3. The nanofluidic biosensor system according to claim 2, wherein the liquid driving subsystem is formed as a layer on at least one of the top substrate and the bottom substrate.

4. The nanofluidic biosensor system according to claim 1, wherein the gas evacuation subsystem is arranged within one or both of the bottom and top substrates.

5. The nanofluidic biosensor system according to claim 1, wherein the gas evacuation subsystem is made of a porous material.

6. The nanofluidic biosensor system according to claim 1, wherein the gas evacuation subsystem includes several crossing through holes that traverse at least one of the bottom and top substrate downstream of the nanoslit.

7. The nanofluidic biosensor system according to claim 1, wherein the bottom and the top substrates are made of a material selected from the group consisting of silicon, glass, plastic, and oxide compounds.

8. The nanofluidic biosensor system according to claim 1, wherein the input and the output lateral apertures have an area between 100 $nm^2$ to 100 $mm^2$, and the nanoslit has a height between 2 nm and 1000 nm, a width between 2 nm and 20 mm, and a length between 2 nm and 20 mm.

9. The nanofluidic biosensor system according to claim 1, wherein the gas evacuation subsystem includes a plurality of crossing-through holes that can be entirely filled by liquid.

10. The method for detecting biomolecules with a nanofluidic system, the nanofluidic system comprising,
a bottom substrate and a top substrate, an input lateral aperture, a nanoslit having a functionalized area, and at least one of an output lateral aperture and an internal reservoir being arranged between the bottom substrate and the top substrate;

a gas evacuation subsystem located between the nanoslit and an external environment of the biosensor downstream from the nanoslit; and an optical system, wherein the method comprises the steps of:

entering a solution having the biomolecules through the input lateral aperture and successively passing the solution through the nanoslit and the at least one of the output lateral aperture and internal reservoir;

evacuating trapped air bubbles by the gas evacuation system; and detecting specific biomolecules immobilized on biomarkers inside the nanoslit by quantifying fluorophores attached to the biomolecules of the solution.

11. The method according to claim 10, wherein the gas evacuation subsystem includes a plurality of crossing-through holes that can be entirely filled by liquid.

12. The method according to claim 10, wherein a liquid driving subsystem is provided between the nanoslit and the gas evacuation subsystem as a layer on at least one of the top substrate and the bottom substrate.

* * * * *